United States Patent [19]
Jeromin et al.

[11] Patent Number: 6,127,561
[45] Date of Patent: Oct. 3, 2000

[54] PROCESS FOR THE PRODUCTION OF MONOGLYCERIDE BASED ON THE GLYCEROLYSIS OF METHYL ESTER

[75] Inventors: Lutz Jeromin, Hilden; Guenter Wozny; Pu Li, both of Berlin, all of Germany

[73] Assignees: Global Palm Products SDN. BHD.; Johor Darul Takzim, Malaysia

[21] Appl. No.: 08/990,004

[22] Filed: Dec. 12, 1997

[30] Foreign Application Priority Data

Aug. 19, 1997 [MY] Malaysia .............................. PI 9703796

[51] Int. Cl.$^7$ ...................................................... C07C 51/00
[52] U.S. Cl. ................................................................ 554/169
[58] Field of Search .............................................. 584/169

[56] References Cited

U.S. PATENT DOCUMENTS

| | | | |
|---|---|---|---|
| 2,909,540 | 10/1959 | Woods | 260/410.7 |
| 3,160,646 | 12/1964 | Steen et al. | 260/410.7 |
| 4,970,892 | 11/1990 | Jeromen et al. | 200/410.7 |

OTHER PUBLICATIONS

Chem abstr, Demmering et al, 96:542628, 1982.
Chem. abstr., Modzelewska et al, 88:39212, 1978.

*Primary Examiner*—Deborah D. Carr
*Attorney, Agent, or Firm*—Smith Gambrell & Russell, LLP.

[57] ABSTRACT

The invention discloses a process for the production of monoglycerides by glycerolysis of methyl ester derived from animal or vegetable fat and oils which includes mixing a surplus of 0.1 to 3 moles of glycerols in relation to methyl ester, subjecting the reaction mixture to a reaction temperature between 130 to 160 at a vacuum of 200 to 400 mbar, adding of alkaline catalysts, stopping the reaction by fast cooling of the reaction mixture and the destruction of the alkaline catalyst when the quantity of glycerides has reached a concentration of mono and diglyceride of 40 to 60%, leaving the catalyst in the reaction mixture to catalyse the reaction downstream in a reactor, separating the surplus methyl ester and glycerol by distillation and stopping the reaction by fast cooling of the reaction mixture with reactor and the destruction of the alkaline catalyst when the quantity of glycerides has reached a concentration of 40 to 60% and the ratio of concentrations of mono and diglyceride lies between 3 to 10.

20 Claims, No Drawings

PROCESS FOR THE PRODUCTION OF MONOGLYCERIDE BASED ON THE GLYCEROLYSIS OF METHYL ESTER

FIELD OF INVENTION

This invention relates to a process for the production of monoglycerides by the transesterification of methyl esters with glycerol.

BACKGROUND OF INVENTION

The new process has several advantages compared with the well-known common processes, which start from the fat itself by transesterification or from fatty acids, by esterification with glycerol. The chemical reaction for the glycerolysis of methyl ester

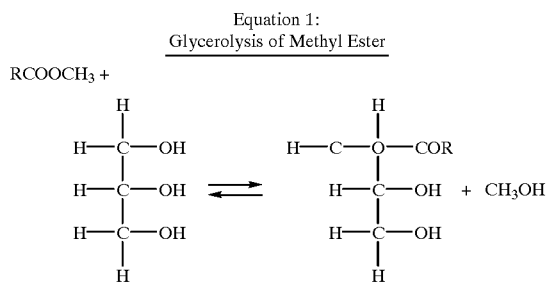

Equation 1:
Glycerolysis of Methyl Ester is reversible and is governed by the Law of Mass Action. The use of excess glycerol and the simultaneous removal of the by-product methanol by vacuum are highly effective in displacing the equilibrium towards the right and hence to high monoglyceride yields. Hereby a 'push-pull' effect will be forced upon the reaction. Fat glycerolysis—in contrast—is only 'push' effective; although it responds to the use of excess glycerol, it does not respond to the application of vacuum except perhaps for the removal of traces of water, if necessary. Methyl ester as a class is far less hydrophobic than triglycerides like fats or fatty acids so that they can be much better emulsified in the glycerol, especially in the presence of monoglyceride. Moreover, a considerable thermal energy advantage and much less thermal degradation of the reaction components favour the methyl ester over fat glycerolysis; for example 130° C. to 160° C. for the methyl ester compared to about 250° C. to 280° C. for fat glycerolysis or the esterification of fatty acids with glycerol.

In general, there is a strong demand to more sophisticated industrial monoglycerides. Methyl esters provides here the opportunity to tailor-make the monoglyceride products to the exact end use requirements, since methyl esters can be fractionated at lower cost by distillation than fatty acids. On the other hand fat glycerolysis can only gain the distribution of the acyl groups in the end products naturally found in fat and oils.

The most important commercial products are glycerol monostearate, monooleate and monoricinoleate. But the vast majority of monoglycerides are applied in various mixtures in the food industry as emulsifiers, diet fat etc. However, there is a large field in technical applications. Due to their ability to form stable emulsions, monooleate is suitable as emulsifying component, for example in fine mechanical oils, as water displacing oils and in grinding and polishing pastes (1). Glycerol monostearate is a well-known plasticiser, lubricant and softener for the processing of technical plastics. These few examples illustrate the necessity to produce monoglyceride tailor made and not a mixture based on several saturated fatty acids or of mixtures of saturated and unsaturated fatty acids as produced by nature.

Equation 1 shows the simplified overall chemical reaction for the glycerolysis of methyl ester to monoglyceride. It is in the sense simplified, since it represents only the main predominant reaction and it does not show the formation of the 2-acyl or β-monoglyceride which cannot be omitted and takes place at every temperature in the order of at least 5 to 8% of the total monoglycerides formed with an increasing tendency up to 20% at higher temperatures (in the order of 250° C.). This phenomenon is due to the known differences in the relative chemical reactivity of primary and secondary hydroxyl groups in direct esterification and transesterification reactions. However, it is observed during the storage of monoglycerides at low temperatures—even in the solid stage—that the β-monoglyceride mostly vanish in favour of the a-monoglyceride during storage.

In general, equation 1 suggests a trimolecular reaction, which is misleading. However, the reaction occurs stepwise, at least in a series of three steps represented by two successive equations with different overall reaction rates. Glycerol and methyl ester reacts initially in a relatively slow reaction depending on the amount of the 'emulsifier' monoglyceride present in the reaction mixture. But unfortunately, there are further equilibrium reactions as shown below, namely to diglyceride and triglyceride:

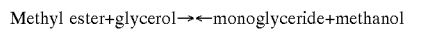
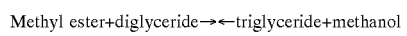

Methyl ester+glycerol→←monoglyceride+methanol

Methyl ester+monoglyceride→←diglyceride+methanol

Methyl ester+diglyceride→←triglyceride+methanol

Apart from these reactions others occur like the transformation of two molecules of monoglycerides forming one molecule of diglyceride and glycerol. Anyway, this reaction series shows qualitatively, that the formation of glycerides occur stepwise starting with the monoglyceride with a preference for the α-position, followed by the diglyceride with a higher content of 1, 2 diglyceride until finally the triglyceride is formed. In every reaction step methanol will be produced. The reaction rate from methyl ester to monoglyceride is much slower than the corresponding one for the transesterification of monoglyceride to diglyceride.

One reason for the different reaction velocities can be seen in the special emulsifying characteristics of the monoglyceride, as Wollman et al (2) for example have shown. Glycerol is neither in methyl ester nor in the glycerides completely soluble, so that always two liquid phases are present at reaction conditions. Monoglyceride is not completely miscible with methyl ester nor with glycerol, but it has due to its structure, a similarity to methyl ester as well as to glycerol and hence excellent emulsifying characteristics in respect of glycerol and methyl ester.

Consequently the mass transfer is best at a high content of monoglyceride leading to high reaction rates from mono- to diglyceride due to the lower mass transfer resistance than for the previous and the subsequent reaction steps. In order to move the reaction equilibrium to glycerides the methanol being formed has to be removed, if a large surplus of glycerol will be avoided.

The reactions are reversible in the range of mutual solubility and are subject to the Law of Mass Action. Hence an excess of glycerol over one mole theoretically required for monoglyceride results in the displacement of the equilibrium to higher monoglyceride concentrations. On the other hand, the excess of glycerol, which remains unaltered in the reaction mixture, must be removed afterwards and thus the Law of Mass Action dictates that the reaction will reverse itself. For this reason, catalyst are in general, but not exclusively, neutralized in order to take advantage of the substantially reduced reaction rates, both forward and backward, of the uncatalyzed system. Thus, at the peak of the monoglyceride formation and hence highest level of monoglyceride content in the reaction mixture, the catalyst must be completely neutralized and the crude reaction mixture cooled down during which time the solubility of the excess glycerol is decreased to such an extent, that some of this excess is thrown out of the solution and separates into two phases; a heavier, mostly glycerol and a lighter, predominantly glycerides containing phase (for further details see (3)).

In complete accord with the Law of Mass Action the whole reaction mixture reaches very rapidly a new equilibrium, especially at high temperatures. In general the content of diglyceride will increase on account mostly of monoglyceride. However, the rate of reversion is much slower than in the case of the catalyzed system. It must be the primary aim to remove the excess of glycerol fast enough and to cool down the reaction mixture quick enough, before a significant reversion can occur. Thus, the catalyst extraction or neutralization together with the removal of the excess glycerol and possibly methyl ester are the key steps for an economical production of monoglyceride. It should be pointed out, that a complete removal or destruction of the catalyst by neutralization is not automatically a guarantee for no outbreak of reversion or rearrangement, respectively, unless cooling and the removal of the surplus amount of glycerol and methyl ester are rapid.

The glycerolysis reaction can be catalyzed by alkaline catalyst like NaOH, KOH, LiOH and $CA(OH)_2$ or sodium salts of lower aliphatic alcohol such as methanol, ethanol, ter-butanol or triols like glycerol. Among those sodium methylate and glycerolate, NaOH or KOH are quite common. In the literature one can find several references to alkaline catalyst function as emulsifiers. These alkali catalyst can generate small quantities of soap from free fatty acids present at least in small quantities in most fats and oils, having in mind the well known emulsifying performance of soap containing mixtures of glycerol and fatty materials. Anyway, emulsification assists reactivity, since the two otherwise nearly immiscible reactants are brought into more intimate contact with one another. The line between the terms 'catalyst' and 'emulsifier' are rather vague and somehow indefinite in glycerolysis, so that it is difficult to distinguish between them.

SUMMARY OF THE INVENTION

The invention discloses a process for the production of monoglycerides by glycerolysis of methyl ester derived from animal or vegetable fat and oils which includes the steps of mixing a surplus of 0.1 to 3 moles of glycerol in relation to methyl ester, subjecting the reaction mixture to a reaction temperature between 130° C. to 160° C. at a vacuum of 200 to 400 mbar, adding alkaline catalysts, and stopping the reaction by fast cooling of the reaction mixture and the destruction of the alkaline catalyst when the quantity of glycerides has reached a concentration of 40 to 60% and the ratio of concentrations of mono and diglyceride lies between 3 to 10. The invention includes the further steps of leaving the catalyst in the reaction mixture to catalyze the reaction downstream in a reactor, separating the surplus methyl ester and glycerol in the reactor and stopping the reaction by fast cooling of the reaction mixture and the destruction of the alkaline catalyst when the quantity of glycerides has reached a concentration of 40 to 60% and the ratio of concentrations of mono and diglycerides lies between 3 to 10. The alkaline catalyst is sodium hydroxide, potassium hydroxide or any one of sodium salts of lower aliphatic alcohol in concentrations of 0.1 to 1% like sodium methylate or sodium glycerolate. The soaps generated by the catalyst are separated from the glyceride mixture by an extraction process with water and split in a subsequent acidulation process with an acid, preferably phosphoric or sulfuric acid, into fatty acids and salts. Where methylates are used as catalyst, the reaction is stopped by the addition of an acid or by the addition of water.

DESCRIPTION OF THE INVENTION

The present invention relates to a process for the glycerolysis of methyl esters based on the above summarized interrelations and sequences. The advantages over the common glycerolysis based on fats and over the esterification of fatty acids with glycerol have been worked out. Suitable starting materials for the present process according to the invention are methyl esters derived from fat and oils of vegetable or animal origin. These methyl esters can be either produced by transesterification of fat and oils or by the esterification of fatty acids with methanol and can afterwards easily separated into different chain lengths by fractional distillation according to the end use requirements. Another possibility is the separation into unsaturated and saturated fractions by well established crystallization processes, like for example the hydrophilization process (4), in order to be able to produce monooleate. Alternatively, all doublebonds could be hardened by hydrogenation processes established for the hardening of fatty acids. Such products are also producible by the esterification of fatty acids with glycerol; but with the disadvantage of their lower thermal stability, so that they are easier subjects of deterioration with resultant impacts on odour and taste.

In the process according to the present invention the methyl ester—either as a mixture or in form of pure fractions—is mixed with glycerol and reacts in the presence of an alkaline catalyst in a thoroughly agitated batch or continuous reactor. The molar ratio of methyl ester to glycerol varies from 1:1 to 1:4, the catalyst concentration lies in the range from 0.1 to 1% based on the amount of methyl ester. The reaction conditions are 120° C. to 200° C. with a preference at 130° C. to 160° C., because this is the limit for the long time thermal stability of glycerol. The pressure in the reactor is adjusted for a quick distillation of the methanol being formed during the reaction and its economical condensation, e.g. in the order of 300 mbar.

The reaction must be stopped near the peak of monoglyceride formation, hence in a range where large amounts of diglyceride are still in acceptable limits caused by consecutive reactions. Since the reaction could further proceed downstream behind the actual reactor, for example in the distillation equipment at even higher temperatures than in the reactor and especially when the catalyst is still present, the stopping criterion must be chosen accordingly taking into consideration all relevant downstream effects. A good criterion to 'freeze' the reaction (molar ratio methyl ester/glycerol 1:1.2 to 1:2) is after having reached a concentration range of 40 to 50% of monoglyceride and less than 10% of diglyceride in order to keep the recycle streams for the diglyceride, for example to the transesterification within acceptable economical limits. At this point the catalyst must be quickly neutralized and the reaction mixture cooled down below 100° C. in order to avoid a re-arrangement of the glycerides with a subsequent increase of the diglyceride concentration. An alternative procedure would be a quick cooling—a form of quench cooling—of the reaction mixture to a temperature as low as possible just avoiding solidification, followed by an extraction of the catalyst with water. This last process has the advantage of keeping the catalyst, soaps in particular, separate and thus avoiding a contamination of the crude reaction mixture with fatty acids after an acidulation of the soaps. These soaps, fatty acids respectively, can cause severe problems in recycle stream as will be shown later.

Consequently the glycerolysis from methyl ester to monoglyceride has to include—besides the actual operations in the reactor—all downstream effects which might lead to a continuation of the reaction or to severe rearrangements between the glycerides. Having these interrelations in mind, the 'freezing' criterion for a maximum yield of monoglyceride with a simultaneous diglyceride concentration below 10% has to be chosen accordingly for the reactor.

If a process alternative is chosen with a neutralization of the catalyst, with phosphorus acid for example, direct after the reaction, the peak of monoglyceride production would certainly lie in the reactor itself. Such a process has the disadvantage, that the soaps being formed from catalysts like NaOH during the glycerolysis will be transferred into fatty acids due to the acidulation. These fatty acids represent a extraneous species in the reaction mixture and complicate the recycle streams of methyl ester and glycerol being produced during the distillation procedures to gain a high monoglyceride concentrate with a purity above 96%. For further details see example (7).

A process variation, which is in particular subject of this invention, overcomes the problems with the fatty acids by leaving the catalyst full in function behind the actual glycerolysis reactor. In the subsequent flash distillation the surplus methyl ester and glycerol will be separated from the glycerides whereby the reaction proceeds even with high velocities because of the higher distillation temperatures in the order of 230° C. depending on the equipment chosen. On the other hand, the distillation equipment must be designed for very short residence times in the order of a couple of minutes to avoid deterioration, especially of the glycerol. Consequently the glycerolysis in the reactor is characterized by low temperatures (130° C. to 160° C.) and long residence times (1 to 2 hours), but in the distillation equipment by high temperatures at about 230° C. and comparable very short residence times in the order of a few minutes.

Based on experimental investigations on laboratory scale the reaction velocities and kinetics in general can be determined depending on the temperature. Based on these data the 'freezing' criterions for the stopping of the reaction will be chosen accordingly in the reactor and the distillation equipment, so that the maximum concentration of monoglyceride in the bottom product stream of the distillation equipment will be reached. Now a very quick cooling of the glyceride stream is essential to avoid an increase of diglyceride on account of the monoglyceride concentration. The next step is the extraction of the catalyst with the help of water for example in a counter current 2-stage mixer-settler apparatus. The catalysts, practically soaps, are washed out with the help of water. In a subsequent acidulation, for example with sulfuric acid, the soaps are converted into fatty acids and sodium sulfate. By this procedure the fatty acids can be kept separately and represent a further product stream.

The glyceride stream will be fractionated in a conventional way into a high monoglyceride product with a purity above 96% and a diglyceride stream containing all residues, which can be recycled to the inlet of the glycerolysis. With this process it is possible to reach even higher purities of the monoglyceride in the order of 97% due to the large relative volatilities between methyl ester and glycerol on one side and the glycerides on the other.

The process alternatives according to the present invention are illustrated with the following examples.

EXAMPLES

Example 1

The experimental set-up consisted of a 500 ml glass reaction vessel equipped with an agitator with adjustable revolution control. The temperature in the reaction vessel was controlled by electrical heating and was adjustable within one degree Celsius. The methanol being formed during the reaction was condensed in a glass condenser cooled with water. A membrane vacuum pump maintained the necessary vacuum at 300 mbar throughout the reaction with the help of a vacuum controller. All experiments described hereafter were carried out batchwise always using the same equipment.

| Reaction mixture: | 272.2 g C16-Methyl Ester (1.01 mol) |
|---|---|
|  | 94.0 g Glycerol (1.02 mol) |
|  | 0.89% Na-Methylate (catalyst) |
| Reaction conditions: | Temperature 130° C. |
|  | Pressure: 300 mbar |
|  | Agitator: 300 Rpm |

Experimental Results

| Sample | 1 | 2 | 3 | 4 | 5 | 6 | 7 |
|---|---|---|---|---|---|---|---|
| Time (min) | 0 | 6 | 27 | 49 | 75 | 113 | 200 |
| Methanol | 0.01 | 0.02 | 0.03 | 0.02 | 0.02 | 0.02 | 0.02 |
| Glycerol | 0.18 | 0.21 | 0.18 | 0.14 | 0.12 | 0.11 | 0.12 |
| C-16 Methyl Ester | 0.81 | 0.73 | 0.62 | 0.40 | 0.33 | 0.32 | 0.23 |

-continued

| | | | | | | | |
|---|---|---|---|---|---|---|---|
| C16-Monoglyc | 0.00 | 0.04 | 0.15 | 0.39 | 0.43 | 0.42 | 0.45 |
| C16-Diglyceride | 0.00 | 0.00 | 0.02 | 0.05 | 0.10 | 0.13 | 0.18 |

Specification of Concentration in (g/g)

If one sets the limit for the maximum acceptable diglyceride concentration with 10%, then the peak of monoglyceride is reached after a reaction time of about 60 minutes with 42%. Consequently the reaction has to be stopped after 55 to 60 minutes under the reaction conditions chosen above.

Example 2

| Reaction Mixture: | 222.8 g C16-Methyl Ester, JZ = 0.5 (0.82 mol) |
| | 92.9 g Glycerol (1.01 mol) |
| | 0.3% Na-Methylate (catalyst) |
| Reaction Conditions: | Temperature 130° C. |
| | Pressure 300 mbar |
| | Agitator 350 Rpm |

Experimental Results

| Sample | 1 | 2 | 3 | 4 | 5 | 6 | 7 | 8 | 9 |
|---|---|---|---|---|---|---|---|---|---|
| Time (min) | 0 | 19 | 58 | 97 | 126 | 141 | 185 | 235 | 260 |
| Methanol | 0.00 | 0.02 | 0.01 | 0.01 | 0.01 | 0.01 | 0.01 | 0.01 | 0.00 |
| Glycerol | 0.29 | 0.11 | 0.14 | 0.17 | 0.07 | 0.10 | 0.12 | 0.14 | 0.11 |
| C16 meth. Est | 0.71 | 0.88 | 0.70 | 0.62 | 0.32 | 0.24 | 0.13 | 0.07 | 0.07 |
| C16 monoglyc | 0.00 | 0.00 | 0.15 | 0.18 | 0.51 | 0.48 | 0.43 | 0.49 | 0.47 |
| C16 diglyc | 0.00 | 0.00 | 0.00 | 0.02 | 0.09 | 0.17 | 0.31 | 0.29 | 0.33 |
| C16 triglc | 0.00 | 0.00 | 0.00 | 0.00 | 0.00 | 0.00 | 0.00 | 0.00 | 0.02 |

For this example the reaction has to be stopped after a reaction time of about 120 minutes to reach a monoglyceride concentration of 50% with a simultaneous diglyceride concentration of 8 to 9%.

Example 3

| Reaction Mixture | 219.1 g Hardened palm Oil Methyl Ester JZ = 0.5, (0.81 mol) |
| | 93.5 g Glycerol (1.02 mol) |
| | 1.0% Na-Methylate (catalyst) |
| Reaction Condition: | Temperature 130° C. |
| | Pressure 300 mbar |
| | Agitator 350 Rpm |

Experimental Results

| Sample | 1 | 2 | 3 | 4 | 5 | 6 |
|---|---|---|---|---|---|---|
| Time (min) | 0 | 11 | 29 | 84 | 110 | 245 |
| Methanol | 0 | 0.01 | 0.03 | 0.01 | 0.01 | 0.01 |
| Glycerol | 0.30 | 0.25 | 0.18 | 0.13 | 0.14 | 0.14 |
| PO Methyl ester | 0.70 | 0.65 | 0.53 | 0.23 | 0.22 | 0.16 |
| PO monoglyceride | 0 | 0.09 | 0.24 | 0.49 | 0.51 | 0.52 |
| PO Diglyceride | 0 | 0 | 0.02 | 0.14 | 0.12 | 0.17 |

(*PO refers to palm oil)

Due to the catalyst concentration of 1% Na-methylate high monoglyceride concentrations above 40% will be reached already after 70 minutes, but the formation of diglycerides will be accelerated as well, so that only a very narrow time corridor can be defined as the criterion for the 'freezing' of the reaction.

Example 4

| Reaction Mixture | 230 g hardened Tallow Methyl Ester, JZ = 0.2 (0.85 mol) |
| | 155 g Glycerol (1.68 mol) |
| | 0.3% Na-Methylate |

-continued

| Reaction Conditions | Temperature 160° C. |
| | Pressure 300 mbar |
| | Agitator 350 Rpm |

Experimental Results

| Sample | | 1 | 2 | 3 | 4 | 5 | 6 |
|---|---|---|---|---|---|---|---|
| Time min | 0 | 37 | 72 | 106 | 155 | 200 | 210 |
| Methanol | 0 | 0.01 | 0.01 | 0.01 | 0.00 | 0.00 | 0.00 |
| Glycerol | 0.40 | 0.30 | 0.26 | 0.25 | 0.24 | 0.23 | 0.21 |
| t. methyl ester | 0.60 | 0.52 | 0.21 | 0.13 | 0.11 | 0.13 | 0.13 |
| t. monoglyceride | 0 | 0.17 | 0.42 | 0.44 | 0.42 | 0.38 | 0.38 |
| t. diglyceride | 0 | 0.01 | 0.10 | 0.17 | 0.23 | 0.26 | 0.28 |

The point to stop the reaction has been reached already after 70 minutes due to the surplus of glycerol and despite the relatively low concentration of catalyst compared with the other examples so far presented.

Example 5

| Reaction Mixture | 235 g Soybean Oil Methyl Ester (0.84 mol) |
| | 156 g Glycerol (1.70 mol) |
| | 0.4% Na-Methylate |
| Reaction Conditions | Temperature 160° C. |
| | Pressure 300 mbar |
| | Agitator 350 Rpm |

-continued

Experimental Results

| Sample | | 1 | 2 | 3 | 4 | 5 | 6 |
|---|---|---|---|---|---|---|---|
| Time (min) | 0 | 35 | 70 | 105 | 156 | 200 | 220 |
| Methanol | 0 | 0.01 | 0.01 | 0.01 | 0.01 | 0.01 | 0.01 |
| Glycerol | 0.40 | 0.31 | 0.24 | 0.22 | 0.23 | 0.21 | 0.21 |
| T methylester | 0.60 | 0.52 | 0.26 | 0.17 | 0.12 | 0.11 | 0.11 |
| T monoglyceride | 0 | 0.15 | 0.41 | 0.47 | 0.42 | 0.40 | 0.39 |
| t. diglyceride | 0 | 0.01 | 0.08 | 0.12 | 0.21 | 0.27 | 0.28 |

Methyl esters produced from unsaturated soybean oil show a similar behavior in the glycerolysis reaction as found for saturated fats and oils. Again the reaction has to be stopped after 70 minutes reaction time to yield a 40% monoglyceride with a simultaneous diglyceride concentration below 10%.

Example 6

| Reaction Mixture | 230 g Hardened Palm Oil Methyl Ester, JZ = 0.5 (0.85 mol) |
| | 160 g Glycerol (1.70) |
| | 0.5% Na-Methylate |
| Reaction Condition: | Temperature 160° C. |
| | Pressure 300 mbar |
| | Agitator 300 Rpm |

Similar to the previous examples a batch reaction has been carried out. However, the reaction was stopped after 50 minutes when the following concentrations have been reached:

1% methanol
40% methyl ester
28% glycerol
26% monoglyceride
5% diglyceride
(0,5% Na-methylate (catalyst)).

Immediately after having stopped the reaction, the mixture—with the catalyst still present was heated up to the distillation temperature of 230° C. and the glycerol and methyl ester separated from the glycerides in a laboratory thin film evaporator (230° C., 4 mbar). The residence time at higher temperatures was estimated to about 4 to 5 minutes. During this time the reaction proceeded further, even strongly accelerated. The bottom product containing:

80% monoglyceride
18% diglyceride
2% residues was immediately cooled down to the extraction temperature of 90° C. At this temperature the catalyst being formed was washed out of the glyceride mixture to enable the common further concentration of the monoglyceride by molecular distillation without severe rearrangements of the glycerides to higher diglyceride or even triglyceride concentrations.

Example 7

The same procedure for the batch reaction as described in the previous example was repeated. Only the catalyst was changed to NaOH using a 10% solution in methanol; the effective catalyst concentration was 0.3% based on the methyl ester. The reaction was stopped after 70 minutes. The analysis carried out later showed the following concentrations:

0,01 % methanol
23% methyl ester
23% glycerol
44% monoglyceride
10% diglyceride

The mixture as immediately neutralized with n/10 phosphoric acid to destroy the reactivity of the catalyst. The soaps being formed during the reaction were split into fatty acids and sodium phosphates. At the same time the reaction mixture was cooled down to 90° C. Despite the prompt neutralization, a re-arrangement of the glycerides could not be avoided since the concentration of diglyceride increased by 2% on account of the monoglyceride.

The reaction mixture contained nearly 3% fatty acids after the neutralization. The fatty acids must be separated before the recycling of the methyl ester and glycerol to the glycerolysis can be initiated. In principle they could be saponified in the recycle stream and used as catalyst for the glycerolysis. However, their catalytical effect is too weak so that fresh Na-methylate must be added leading to an accumulation of the soaps, fatty acids respectively.

Consequently, the only economical way to get rid of the fatty acids is to transform them into soaps, to extract them and to proceed as shown in Example 6.

Those skilled in the art will appreciate that the invention described herein is susceptible to variations and modifications other than these specifically described. It is to be understood that the invention includes all such variations and modifications.

The inventions also includes all of the steps, features, compositions and compounds referred to or indicated in this specifications, individually or collectively, and any all combinations of any two or more of said steps or

| Literature | |
|---|---|
| 1. Meffert, A: | Technical uses of fatty acid esters |
| | J. Am. Oil Chem. Soc. 61 (1984), 255 |
| 2. Wollmann, G: | Glycerolysis—design of chemical reaction of |
| Gutsche, B. | immiscible liquids |
| Peukert, E | Fat Sci. Technol. 90 (1988), 507 |
| Jeromin, L | |
| 3. Sanchez N. | Selective esterification of glycerine to glycerol |
| Martinez, M | monooleate. 1. Kinetic modeling |
| Aracil, J | Ind. Eng. Chem. Res. 36 (1997), 1524 |
| 4. Dieckelmann, G. | The basics of industrial oleochemistry |
| Heinz, H. | Press Peter Pomp GmbH, Essen 1988 |
| | ISBN 3-89355-008-9 |

What is claimed is:

1. A process for the production of monoglycerides by glycerolysis comprising:
   i) reacting methyl ester derived from animal or vegetable fat and oils by mixing a surplus of 0.1 to 3 moles of glycerol in relation to methyl ester;
   ii) subjecting the reaction mixture to reaction temperature between 130° to 160 ° C. at a vacuum of 200 to 400 mbar;
   iii) adding alkaline catalysts; and iv) stopping the reaction by fast cooling of the reaction mixture and the destruction of the alkaline catalyst when the quantity of glycerides has reached a concentration of 40 to 60% and the ratio of concentrations of mono and diglyceride lies between 3 to 10.

2. A process as claimed in claim 1 including further steps of:
   (i) leaving the catalyst in the reaction mixture to catalyze the reaction downstream in a reactor;
   (ii) separating the surplus methyl ester and glycerol in the reactor;
   (iii) stopping the reaction by fast cooling of the reaction mixture and the destruction of the alkaline catalyst when the quantity of glycerides has reached a concentration of 40 to 60% and the ratio of concentrations of mono and diglyceride lies between 3 to 10.

3. A process as claimed in claim 1 wherein the alkaline catalyst is sodium hydroxide, potassium hydroxide, or any one of sodium salts of lower aliphatic alcohol in concentrations of 0.1 to 1%.

4. A process as claimed in claim 1 wherein the sodium salt of lower aliphatic alcohol is sodium methylate or sodium glycerolate.

5. A process as claimed in claim 1 wherein the ratio of the concentrations of mono and diglyceride lies between 4 to 8.

6. A process as claimed in claim 1 in which soaps generated by the catalyst are separated from the glyceride mixture by an extraction process with water, and split in a subsequent acidulation process with an acid, preferably phosphoric or sulfuric acid, into fatty acids and salts.

7. A process as claimed in claim 1 in which the reaction is stopped by the addition of an acid or by the addition of water in the case of methylates to inactivate the catalyst.

8. A process as claimed in claim 1 in which the methyl ester is fractionated in different carbon numbers and according to end use necessities of the monoglycerides.

9. A process as claimed in claim 1 in which the methyl ester is separated in saturated and unsaturated species by crystallization processes according to end use requirements.

10. A process as claimed in claim 1 in which the unsaturated species of methyl esters are hydrogenated (hardened) to gain a fully saturated raw material for the glycerolysis.

11. A process as claimed in claim 8 in which the fractionation and crystallization are combined.

12. A process as claimed in the claim 8 in which the fractionation and hydrogenation are combined.

13. A process as claimed in the claim 9 in which the crystallization and hydrogenation are combined.

14. A process as claimed in claim 1 in which monoglyceride is recycled to the inlet of the glycerolysis to increase the reaction velocities.

15. A process as claimed in claim 1 wherein the vegetable oil is palm oil.

16. Monoglycerides produced according to any of claim 1.

17. Monoglycerides produced according to any of the claim 1 from palm oil.

18. A process as claimed in claim 3 wherein the sodium salt of lower aliphatic alcohol is sodium methylate of sodium glycerolate.

19. A process as claimed in claim 9 in which the fractionation and crystallization are combined.

20. A process as claimed in claim 10 in which the fractionation and hydrogenation are combined.

* * * * *